US00PP30053P3

(12) United States Plant Patent
Danziger

(10) Patent No.: US PP30,053 P3
(45) Date of Patent: Jan. 1, 2019

(54) ***SALVIA* PLANT NAMED 'DSALMAGWAN'**

(50) Latin Name: *Salvia hybrida*
Varietal Denomination: DSALMAGWAN

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/731,258

(22) Filed: May 10, 2017

(65) Prior Publication Data

US 2018/0332757 P1 Nov. 15, 2018

(51) Int. Cl.
*A01H 5/02* (2018.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Cassandra Bright

(57) ABSTRACT

A new and distinct *Salvia* cultivar named 'DSALMAGWAN' is disclosed, characterized by a sturdy plant form that remains upright, resisting lodging. Flowering occurs continuously from Spring to Fall and plants exhibit great performance in heat and humidity. The new variety is a *Salvia*, normally produced as an outdoor garden or container plant.

2 Drawing Sheets

Figure 1:
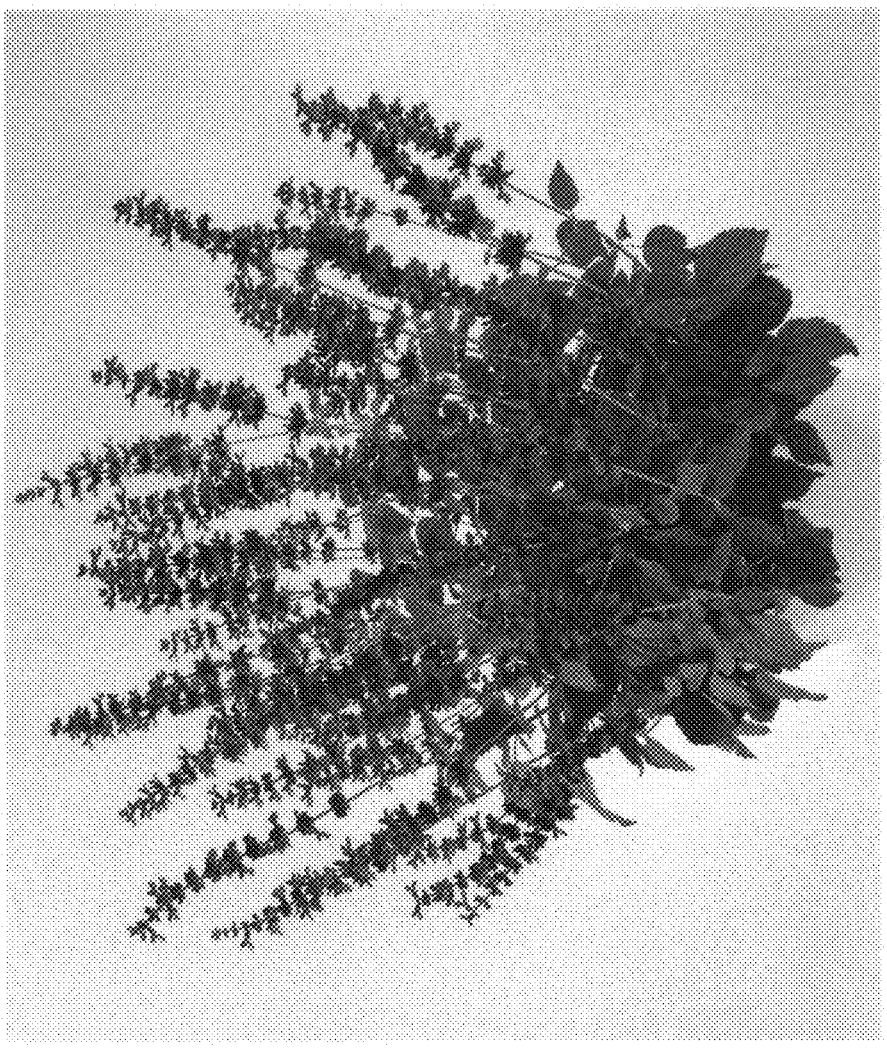

Latin name of the genus and species: *Salvia hybrida.*
Variety denomination: 'DSALMAGWAN'.

BACKGROUND OF THE INVENTION

The new *Salvia* cultivar is the product of a planned breeding program conducted by the inventor, Gavriel Danziger, in Moshav Mishmar Hashiva, Israel. The objective of the breeding program was to produce new *Salvia* varieties for ornamental commercial applications. The open pollination resulting in this new variety was made during 2011.

The seed parent is an, unpatented, unnamed proprietary *Salvia hybrida*. The pollen parent is unknown as it was an open pollination breeding program. The new variety was discovered in May of 2012 by the inventor in a group of seedlings resulting from the 2011 open pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in May of 2012 and has shown that the unique features of this cultivar are stable and reproduced true to type in multiple successive generations.

SUMMARY OF THE INVENTION

The cultivar 'DSALMAGWAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSALMAGWAN' These characteristics in combination distinguish 'DSALMAGWAN' as a new and distinct *Salvia* cultivar:

1. Sturdy plant remains upright without falling open, resisting lodging.

2. The new variety blooms constantly from Spring through Fall
3. The new variety has great performance in heat and humidity

PARENTAL COMPARISON

Plants of the new cultivar 'DSALMAGWAN' are similar to plants of the seed parent, in most horticultural characteristics, however, plants of the new cultivar 'DSALMAGWAN' differ in the following;

1. The new variety has a more compact habit than the seed parent.
2. The new variety has a darker flower color.
3. The new variety has a shorter flower inflorescence.

COMMERCIAL COMPARISON

Plants of the new cultivar 'DSALMAGWAN' are comparable to the unpatented commercial variety *Salvia* 'Indigo Spires'. The two *Salvia* varieties are similar in most horticultural characteristics; however, the new variety 'DSALMAGWAN' differs in the following:

1. The new variety has a more compact and spreading habit compared to 'Indigo Spires'.
2. The new variety has more inflorescences per plant than 'Indigo Spires'.
3. The new variety has a shorter inflorescence than 'Indigo Spires'.

Plants of the new cultivar 'DSALMAGWAN' can also be comparable to the unpatented commercial variety *Salvia* 'DANSALFUN1' U.S. Plant Pat. No. 19,788. The two *Salvia* varieties are similar in most horticultural characteristics; however, the new variety 'DSALMAGWAN' differs in the following:

1. The new variety has larger flowers than 'DANSALFUN1'.

2. The new variety grows more vigorously than 'DANSALFUN1'
3. The new variety has darker violet colored flowers than 'DANSALFUN1', which has lighter violet flowers.

BRIEF DESCRIPTION OF THE PHOTOGRAPHS

The accompanying photograph in FIG. 1 illustrates in full color a typical plant of 'DSALMAGWAN' grown in 15 cm pots outdoors in Moshav Mishmar Hashiva, Israel.

Figure 2:
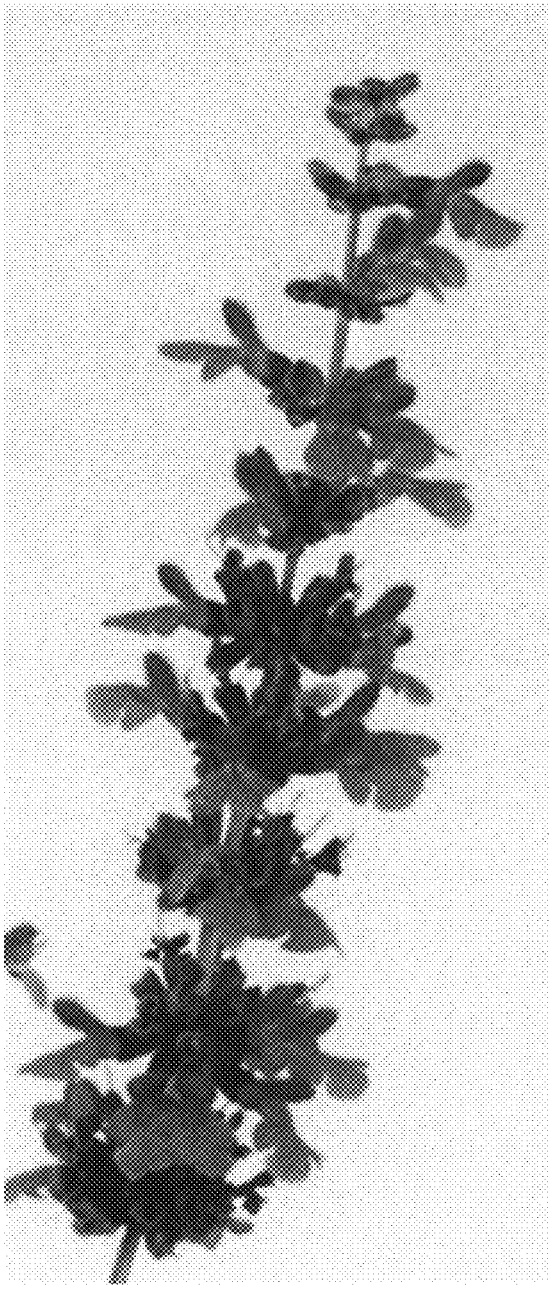

FIG. 2 illustrates in full color a close up view of a typical inflorescence of 'DSALMAGWAN'. Age of the plant photographed is approximately 4 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DSALMAGWAN' plants grown in the Autumn, to Spring in moderate climate in a greenhouse, in Moshav Mishmar Hashiva, Israel. during the night. General light conditions are bright, normal sunlight. Measurements and numerical values represent averages of typical plant types.

Botanical classification: *Salvia hybrida* 'DSALMAGWAN'.

PROPAGATION

Type of propagation typically used: Vegetative cutting.
Time to initiate roots: 6-8 days at approximately 18-24° C.
Time to produce a rooted cutting: About 14 days at 18-24° C.
Root description: Moderately dense and fibrous. Medium brown in color, not accurately measured with R.H.S. chart.

PLANT

Overall plant shape or growth habit: Compact, spreading and upright.
Plant spread: Approximately 50 cm.
Plant height: Approximately 50 cm.
Growth rate: Moderate to fast.
Length of primary lateral branches: Approximately 50 cm.
Diameter of lateral branches: Approximately 0.4 cm
Quantity of lateral branches: About 8 to 10.
*Color*.—Near Yellow-green group 146B.
*Texture/pubescence*.—Lightly pubescent with soft, short featherlike hairs, slightly ribbed longwise.
Internode length: Approximately 2.5 cm.
Age of plant described: Approximately 15 weeks from a rooted cutting.

FOLIAGE

Leaf:
*Arrangement*.—Opposite.
*Quantity*.—Approximately 30-50 per main branch.
*Average length*.—Approximately 5 cm.
*Average width*.—Approximately 4 cm.
*Shape of blade*.—Obovate.
*Apex*.—Apiculate.
*Base*.—Truncate.
*Attachment*.—Petiolate.
*Margin*.—Serrate.
*Undulation*.—Weak.
*Texture of top surface*.—Lightly pubescent with soft, short featherlike hairs. Rugose due to venation.
*Texture of bottom surface*.—Highly pubescent with soft, short featherlike hairs Rugose due to venation.
*Color*.—Young foliage upper side: Near Green 137A. Young foliage under side: Near Yellow-green 147B. Mature foliage upper side: Near Yellow-green 147A. Mature foliage under side: Near Yellow-green 147B.
*Venation*.—Type: Anastomosing. Venation color upper side: Near Yellow-green 146B. Venation color under side: Near Yellow-green 147B.
*Petiole*.—Average Length: Approximately 2 cm. Diameter: Approximately 0.1 cm. Color: Near Yellow-green 146B.

FLOWER

Natural flowering season: From early Spring to late Autumn in Israeli conditions or similar Mediterranean conditions.
Inflorescence type and habit: Bilabiate flowers arranged in verticillasters on spike, upright.
Flower longevity on plant: About 3 to 5 days, depending on temperature; flowers persistent.
Quantity of flowers: About 26-38 blooming spikes per plant.
Inflorescence size:
*Diameter*.—Approximately 4 cm.
*Height*.—Approximately 30 cm.
*Flowers and buds per inflorescence*.—Approximately 20.
Peduncle:
*Length*.—6 cm.
*Diameter*.—0.4 cm.
*Texture*.—Lightly pubescent with soft, short feathers like hairs.
*Color*.—Near Yellow-green 146A.
*Orientation*.—About 30° from vertical.
*Strength*.—Strong.
*Petal arrangement*.—The corolla is sympetalous and typically bilabiate with 2 small, highly fused lobes forming an upper lip and 3 larger highly fused lobes forming a lower lip.
Individual Flowers:
Size:
Upper lip (tube like forming):
*Diameter*.—Approximately 0.5 cm.
*Length*.—Approximately 0.5 cm.
Lower lip (4 fused lobe):
*Length*.—Approximately 1 cm.
*Width*.—Approximately 1 cm.
*Persistence*.—Non-persistent.
*Fragrance*.—Very sweet, nectar-like fragrance.
Petals: One upper lip and one lower lip with 4 lobes. Lips are fused at base. Upper lip has smooth short feather like hairs, lower lip is smooth and hairless.
*Tip shape*.—Upper lip: Obtuse. Lower lip: Blunt.
*Length*.—Upper lip: 0.5 cm. Lower lip: 1 cm. Tube: 0.8 cm.
*Width*.—Upper lip: 0.4 cm. Lower lip: 1 cm. Tube: 0.2 cm.
*Texture*.—Upper lip: Smooth short featherlike hairs. Lower lip: Smooth and non-pubescent. Tube: Smooth.

Color:

*Upper lip*.—When opening: Inner surface: Near Violet-blue 93B. Outer surface: Near Violet-blue N89A. Fully opened: Inner surface: Near Violet-blue 96C. Outer surface: Near Violet-blue 95A. Fading: Inner surface: Near Violet-blue 95C. Outer surface: Near Violet-blue 95A.

Color:

*Lower lip*.—When opening: Inner surface: Near Violet-blue 93C. Outer surface: Near Violet-blue N89C. Fully opened: Inner surface: Near Violet-blue 94C. Outer surface: Near Violet-blue 94A. Fading: Inner surface: Near Violet-blue 96A. Outer surface: Near Violet-blue 94B.

Color:

*Tube*.—When opening: Inner surface: Near Violet-blue 91A. Outer surface: Near Violet-blue 97A. Fully opened: Inner surface: Near Violet-blue 93D. Outer surface: Near Violet-blue 93B. Fading: Inner surface: Near Violet-blue 94A. Outer surface: Near Violet-blue 93B.

Bud:

*Shape*.—Ovoid.
*Length*.—0.5 cm.
*Diameter*.—0.3 cm.
*Color*.—Near Violet-blue 93A.

Sepals:

*Shape*.—2 lobes fused at base to form a tube.
*Quantity per flower*.—2.
*Length*.—Approximately 0.7 cm.
*Width*.—Approximately 0.4 cm.
*Margin*.—Entire.
*Texture*.—Featherlike hairs, with rough lines longwise.
*Color*.—Near Violet-blue N92B.

REPRODUCTIVE ORGANS

Stamens:

*Number*.—2.
*Filament length*.—Approximately 0.2 cm.

Anthers:

*Shape*.—Obovate.
*Length*.—Approximately 0.2 cm.
*Color*.—Outer: Near Violet-blue 90A. Inner: Near Yellow-orange 22A.
*Pollen*.—Not detected.

Pistil:

*Number*.—1.
*Length*.—Approximately 1.6 cm.
*Style*.—Length: Approximately 1 cm. Color: Near Violet-blue 92D.
*Stigma*.—Shape: V shape with one side longer than the other. Color: Near Violet-blue 94A. Ovary color: Near Yellow 3C.

OTHER CHARACTERISTICS

Seeds and fruits: Not observed to date.

Disease/pest resistance: Neither resistance nor susceptibility to normal diseases and pests of *Salvia* has been observed.

Temperature tolerance: Temperature range: Observed to tolerate temperatures from 5° C. to at least 40° C.

Drought tolerance: Not tolerant to drought.

Environmental tolerance: Tolerates both heat and humidity well and resists lodging in wind and rain.

What is claimed is:

1. A new and distinct cultivar of *Salvia* plant named 'DSALMAGWAN' as herein illustrated and described.

* * * * *